(12) United States Patent
Roberts et al.

(10) Patent No.: US 11,145,406 B2
(45) Date of Patent: Oct. 12, 2021

(54) SYSTEMS AND METHODS FOR MANAGING CARE TEAMS

(71) Applicant: CERNER INNOVATION, INC., Kansas City, KS (US)

(72) Inventors: Andrew Roberts, Overland Park, KS (US); Sasanka Are, Kansas City, MO (US); Janae Lenox, Kansas City, MO (US); Bryce Schaffter, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 260 days.

(21) Appl. No.: 16/046,579

(22) Filed: Jul. 26, 2018

(65) Prior Publication Data

US 2019/0035502 A1 Jan. 31, 2019

Related U.S. Application Data

(60) Provisional application No. 62/537,033, filed on Jul. 26, 2017.

(51) Int. Cl.
*G16H 40/20* (2018.01)
(52) U.S. Cl.
CPC .................................. *G16H 40/20* (2018.01)
(58) Field of Classification Search
CPC ........ G16H 50/20; G16H 50/30; G16H 50/50; G16H 40/20
USPC ............................................................. 705/2
See application file for complete search history.

(56) References Cited

U.S. PATENT DOCUMENTS

| 2012/0245948 | A1 | 9/2012 | Nolte et al. | |
| 2012/0253836 | A1* | 10/2012 | Nolte | G16H 40/20 705/2 |
| 2014/0122100 | A1 | 5/2014 | Fillmore | |
| 2015/0012298 | A1* | 1/2015 | Ash | G16H 10/60 705/3 |
| 2016/0092641 | A1 | 3/2016 | Delaney et al. | |

(Continued)

FOREIGN PATENT DOCUMENTS

| WO | WO-2015023674 A1 * | 2/2015 | ............. G16H 50/20 |
| WO | WO-2018044807 A1 * | 3/2018 | ............. G16H 40/20 |

OTHER PUBLICATIONS

Preinterview First Office Action received for U.S. Appl. No. 16/235,725, dated Aug. 24, 2021, 4 pages.

*Primary Examiner* — Hiep V Nguyen
(74) *Attorney, Agent, or Firm* — Shook, Hardy & Bacon L.L.P.

(57) ABSTRACT

Methods and systems for managing care team assignment's for individuals, such as a patient, are provided. Embodiments include receiving indicators of actions that are initiated by a clinician and associated with a patient's care. Using times associated with each action, a time series indicating contribution levels for each clinician may be constructed. Care contribution curves measuring a clinician's care contribution level over time may be generated using the time series and a rate of decay for each action, which may be based on the type of action and the role of the clinician who initiated the action. A care contribution score for each clinician may be determined from the clinician's care contribution curve, and a care team assignment for the patient may be created based on care contribution scores for each clinician who initiated an action.

20 Claims, 13 Drawing Sheets

(56) References Cited

U.S. PATENT DOCUMENTS

2017/0185723 A1 6/2017 Mccallum et al.
2018/0150604 A1 5/2018 Arena et al.

\* cited by examiner

| | NAME | PID | ROLE | SPEC | NORM.CONTRIBUTION | TOT.ORDERS | N.ORDERS | TOT.EVENTS | N.EVENTS | TOT.DXS | N.DXS | TOT.CHARTS | N.CHARTS |
|---|---|---|---|---|---|---|---|---|---|---|---|---|---|
| 1 | CARDIO 1 | 1234ABC | PHYSICIAN | CARDIO | 0.663 | 61 | 15 | 0 | 0 | 0 | 0 | 8 | 8 |
| 2 | ONC 1 | 5678DEF | PHYSICIAN | ONCOLOGY | 0.350 | 8 | 3 | 0 | 0 | 2 | 1 | 4 | 4 |
| 3 | CARDIO2 | 9012GHI | PHYSICIAN | CARDIO | 0.248 | 13 | 1 | 0 | 0 | 2 | 2 | 6 | 6 |
| 4 | EMERGENCY | 3456CBA | PHYSICIAN | EMERGENCY | 0.186 | 13 | 3 | 0 | 0 | 0 | 0 | 8 | 8 |
| 5 | ONC2 | 7890FED | PHYSICIAN | ONCOLOGY | 0.010 | 0 | 0 | 0 | 0 | 0 | 0 | 1 | 1 |

FIG. 6C.

| | NAME | PID | ROLE | SPEC | NORM.CONTRIBUTION | TOT.ORDERS | N.ORDERS | TOT.EVENTS | N.EVENTS | TOT.DXS | N.DXS | TOT.CHARTS | N.CHARTS |
|---|---|---|---|---|---|---|---|---|---|---|---|---|---|
| 1 | CARDIO 1 | 1234ABC | PHYSICIAN | CARDIO | 0.663 | 61 | 15 | 0 | 0 | 0 | 0 | 8 | 8 |
| 2 | ONC 1 | 5678DEF | PHYSICIAN | ONCOLOGY | 0.350 | 8 | 3 | 0 | 0 | 2 | 1 | 4 | 4 |
| 3 | EMERGENCY 1 | 3456CBA | PHYSICIAN | EMERGENCY | 0.186 | 13 | 3 | 0 | 0 | 0 | 0 | 8 | 8 |

660

SYSTEMS AND METHODS FOR MANAGING CARE TEAMS

CROSS-REFERENCE TO RELATED APPLICATIONS

This application claims the benefit of U.S. Provisional Application No 62/537,033 titled "SYSTEM AND METHOD FOR MANAGING CARE TEAMS," filed on Jul. 26, 2017, which is hereby expressly incorporated by reference in its entirety.

BACKGROUND

Care teams are groups of individuals who coordinate their efforts to support the health of a person, such as a patient, for a particular time period or throughout the person's lifetime. Care team assignments are used to provide a patient and other individuals with an understanding of who is caring for the patient and which role each care team member has. Because care team assignments are used by the patient or other health providers to identify the responsible team members when issues or questions arise, adequate assignment is important. Assignment of the care team is often done manually through self-designation by the clinician or by another person overseeing care team assignments. Manual assignments, however, often result in an inaccurate or incomplete assignment of a patient's care team because initial assignments may not accurately reflect who is actually contributing most to the patient's care, especially as the person's needs and the management of the person's health care evolve over time. Additionally, clinicians sometimes do not have assignments created, which also results in an incomplete assignment of the care team.

SUMMARY

Systems, methods and computer-readable media are provided for creating or determining care team assignments for a patient that accurately reflect individuals who are involved with and have responsibility over the patient's care and, in some aspects, using the care team assignments for notifying appropriate clinicians of the patient's condition or for performing other actions. In particular, a care team assignment system is provided for generating care team assignments based on clinicians' interactions with a patient and/or the patient's care process, including ranking clinicians based on the relative degree that each clinician contributed to the patient's care.

Embodiments automatically track clinicians' interactions with the patient and attribute a care contribution level for each interaction. The care contribution level for an action may decay over time, and, in some embodiments, a particular rate of decay may be determined by the type of action taken and the role of the clinician who took the action. Care contribution curves generated using the times the actions were taken and the rates of decay may be used to determine care contribution scores for each clinician. The clinicians may be ranked using the care contribution scores within the clinician's role and, in some aspects, the clinician's specialty, and a care team is determined based on the ranking. One aim of the disclosure is to provide an accurate and up-to-date representation of a patient's care team and, in some aspects, notify care team members of events within the patient's condition. Other embodiments may suggest or recommend care team members based on the care contribution scores and/or use the suggestions to assess the adequacy of existing care team assignments. Additionally, the care team assignments may be used in conjunction with information regarding the patient's outcome to optimize care team compositions and patient care for increasing the likelihood of better outcomes in the future.

BRIEF DESCRIPTION OF THE DRAWINGS

The present invention is described in detail below with reference to the attached drawing figures, wherein:

FIG. 6C-D depict graphical representations of the care contributions for a group of potential care team members, in accordance with an embodiment of the disclosure;

DETAILED DESCRIPTION

Figure 1A:
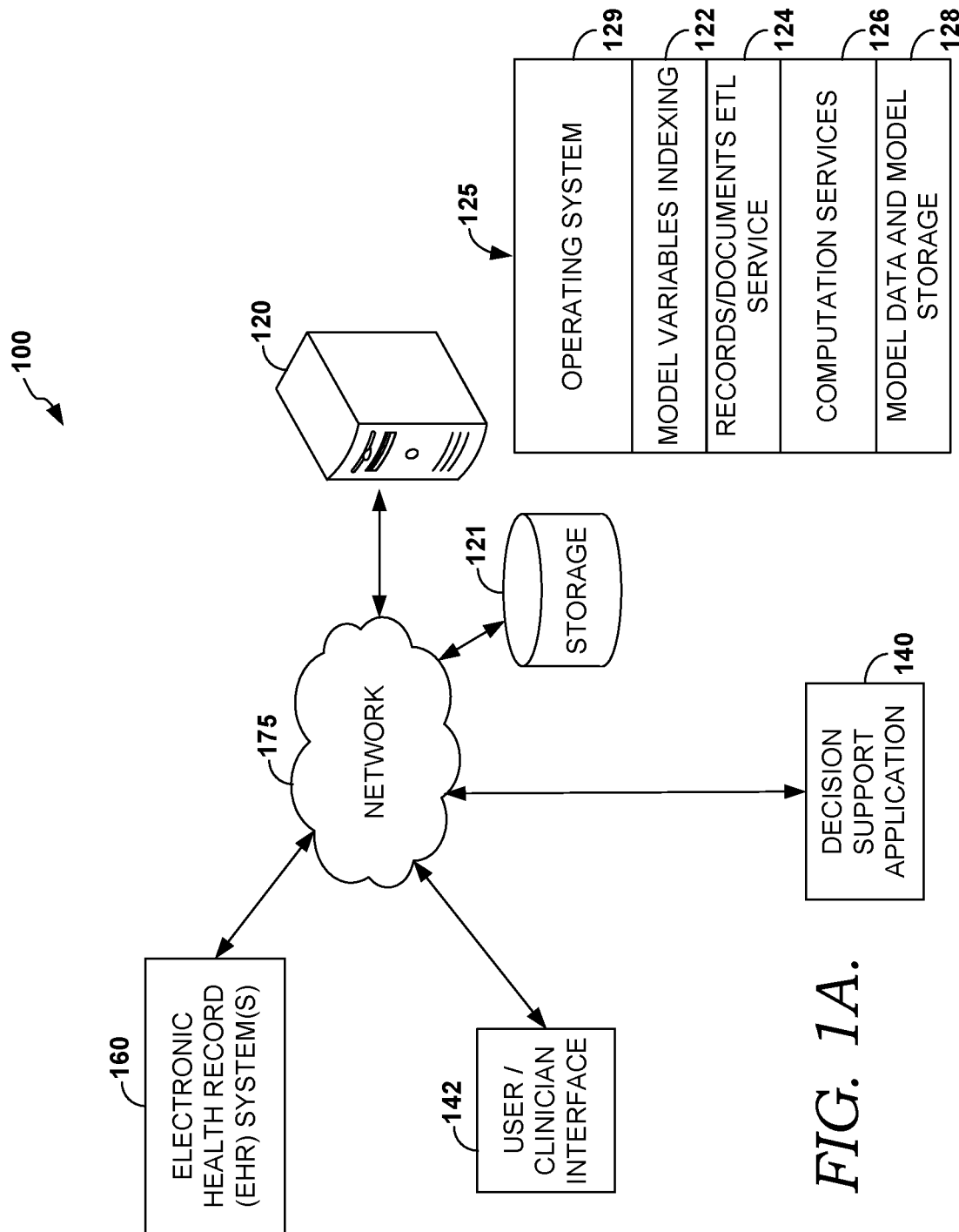
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1A-1B.

Accordingly, at a high level, this disclosure describes, among other things, methods and systems for creating care team assignments for a patient. In some embodiments, the methods and systems may be implemented as a decision support computer application or tool and may be part of a more comprehensive healthcare decision support application for monitoring patients and providing decision support to caregivers. Such decision support technology plays an important part of modern care processes for a patient. Embodiments described herein assign clinicians to a patient's care team based on tracking interactions with a patient or the patient's care, which provides an accurate representation of clinicians who are contributing to a patient's care in a way that would place responsibility on the clinicians. Some embodiments of the decision support tool further use the care team assignments to determine the appropriate clinicians responsible for the patient's care and notify the appropriate clinicians of a clinical event. Other embodiments further measure the adequacy of existing care team assignments in light of the care team assignments suggested based on the care contribution scores or learn from care team compositions and actions performed within the care process to optimize patient outcomes.

In particular, embodiments include receiving indicators of actions that are initiated by a clinician and associated with a patient's care. Example actions include viewing a patient's chart, entering documentation into the patient's chart, entering or updating a diagnosis, or ordering a lab or medication. Each indicator received identifies a time that an action is taken and at least one clinician associated with the action. Over the course of a patient's encounter, indicators of actions associated with multiple clinicians may be received, and each clinician may be considered a potential care team member. For each potential care team member, a time series of the actions taken by the clinician for the patient over a period of time may be constructed. An initial care contribution level may be assigned for each action. A care contribution curve measuring a clinician's care contribution level over time may be generated using the initial care contribution level and a rate of decay for each action. The rate of decay is a decrease in the care contribution level associated with the action over time and may be based on the type of action and the role of the clinician who initiated the action. A care contribution score for a clinician may be determined from the care contribution curve and the time series, and a care team assignment for the patient may be created or otherwise determined based on care contribution scores for each clinician who initiated an action for the patient's care. In some aspects, the care contribution score is the area under the care contribution curve over the period of time.

Accordingly, one aim of embodiments of this disclosure relates to deriving appropriate care team assignments that accurately represent who should be responsible for the patient's care based on previous interactions involving the patient. A care team generally refers to individuals who coordinate their efforts to support the health of a person, such as a patient, for a particular time period or throughout the person's lifetime. The care team may include clinical and non-clinical members. Clinical members may include, for example, physicians, physician assistants, nurse practitioners, registered nurses, behavior specialists, respiratory therapists, physical therapists, radiologists, care managers, patient care technicians, pharmacists, health information manager, and the like.

There often are several clinicians who have taken some action for a particular patient, but an assigned care team includes individuals who are primarily responsible for the patient. The assignment of the care team is often used by the patient or the patient's healthcare provider, including physicians and care managers, to determine who is responsible for the patient's care. For instance, when a patient has a question about his or her care, the patient may refer to the care team assignment to determine who to contact. Similarly, when another clinician, such as a nurse, notices an issue with the patient, the clinician may determine who to notify based on the care team assignment.

Currently, a patient's care team is generated based on a manual assignment, which may include self-designation or manual additions by the clinicians themselves. This manual method of producing a representation of a patient's care team is not always accurate because, sometimes, there are clinicians who are not directly assigned to the patient but who end up contributing significantly to the patient's care without manually assigning themselves. Further, there may be multiple members with similar roles who work on a patient's care and are assigned to the care team but who do not contribute at the same level; however, the current method of care team assignment does not involve quantifying each member's contribution in a way to determine which member is the more responsible for the patient's care. Additionally, even if a care team is updated to reflect changes to care team members, these updates are not always done in a timely manner through manual assignment. An accurate representation of a care team is important to a patient's understanding of who is caring for them and which role each care team member has. It is also important to the care team members or other employees of a healthcare provider or facility as a reference of who to contact regarding that specific patient.

Accordingly, embodiments of the disclosure as described herein improve upon conventional industry practice by measuring each potential team member's contributions in a quantifiable and objective way to provide a more accurate representation of the care team for more effective and efficient treatment and care. Embodiments receive electronic indications of an interaction with a patient and, based on the type of interaction and role of the clinician involved in the interaction, rank clinicians who are most responsible for the patient to assign or recommend a care team for the patient. Specifically, when an action, such as reviewing a patient's chart, placing an order, adding documentation to the patient's EHR, or entering or updating a diagnosis, is logged, a care contribution curve for a clinician associated with the action is altered based on the type of action and the role of the clinician. A care contribution score is determined from the care contribution curve and used to rank clinician's involvement. A care team may be assigned or recommended based on the care contribution scores of each clinician. Additionally, updates to the patient's care based on new actions may be automatically performed by embodiments of the present technologies to assess the care team composition in real time, which provides for an accurate representation to provide more efficient care when a care member is needed.

Further, in some aspects, the actions that trigger assignment or reassignment of care team members may already be actions documented in the patient's EHR or otherwise electronically tracked such that no additional steps outside of the usual care protocol need to be taken by clinicians or staff. Although the information may be already documented, this information represent new sources of information for creating care team assignments that are not used in convention systems. Utilizing these non-conventional sources of information to generate care curves provides is a non-conventional technique in assigning care teams and allows for a more accurate and updated representation of the appropriate care team for a given patient In some embodiments, the present disclosure is utilized for suggesting care team assignments and assessing the adequacy of care team assignments created with other methods, such as manual assignment, in light of the suggested assignments. Further, embodiments may also be used to optimize care team assignments by determining the care team compositions, either by role/specialty or by individual clinician, that have better patient outcomes than other care team compositions. Additionally, the frequency for performing actions that is associated with better patient outcomes may be determined.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural). Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer-readable media having machine-readable application software embodied thereon. In this regard, a machine-readable storage media may be any tangible medium that can contain, or store a software application for use by the computing apparatus.

As shown in FIG. 1A, example operating environment 100 provides an aspect of a computerized system for compiling and/or running an embodiment of a computer-decision support tool for creating a care team assignment for a patient based on clinician interactions with the patient. Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, the functions performed by these components, or the services carried out by these components may be implemented at appropriate abstraction layer(s), such as the operating system layer, application layer, hardware layer, etc., of the computing system(s). Alternatively, or in addition, the functionality of these components and/or the embodiments described herein can be performed, at least in part, by one or more hardware logic components. For example and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that, in some embodiments, functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems, and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the technologies described herein, sequence itemset mining is performed using data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, the acute or chronic nature of the health conditions that pertain to the patient, the rate of change of the severity of the health conditions, or other factors. Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks, such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health-related records, which may be stored on storage 121, and may further include one or more computers or servers that facilitate the storing and retrieval of the health records. In some embodiments, EHR system 160 and/or other records systems may be implemented as a cloud-based platform or may be distributed across multiple physical locations. EHR system 160 may further include record systems, which store real-time or near real-time patient (or user) information, such as wearable sensor or monitor, bedside, or in-home patient monitors or sensors, for example. Although FIG. 1A depicts an example EHR system 160, it is contemplated that an embodiment relies on decision support application 140 for storing and retrieving patient record information.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet and may be used to provide or manage user services provided by an embodiment of the technologies described herein, which may be used by a caregiver to provide, for example, information about the care team assignment, including suggestions for care team assignments. In some embodiments, application 140 includes or is incorporated into a computerized decision support tool, as described herein. Further, some embodiments of application 140 utilize user/clinician interface 142.

In some embodiments, application 140 and/or interface 142 facilitate accessing and receiving information from a user or healthcare provider about a specific patient or set of patients, according to the embodiments presented herein. Embodiments of application 140 also may facilitate accessing and receiving information from a user or healthcare provider and facilitates the display of results, recommendations, or orders, for example. The information accessing, received and/or displayed includes information about a specific patient, caregiver, or population including historical data; healthcare resource data; variables measurements, time series, and care team assignments described herein; or other health-related information. In an embodiment, application 140 also facilitates receiving orders, staffing scheduling, or queries from a user based on the results of monitoring patient interactions for determining care contributions from each clinician, which may, in some embodiments, utilize user interface 142. Decision-Support application 140 may also be used for evaluation of the performance of various embodiments.

In some embodiments, user/clinician interface 142 may be used with application 140, such as described above. One embodiment of user/clinician interface 142 comprises a user interface that may be used to facilitate access by a user (including a healthcare provider or patient) to a suggested or assigned care team for a patient. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application, which may take the form of an applet or app, or a set of applications usable to manage user services provided by an embodiment of the technologies described herein.

In some embodiments, interface 142 may facilitate providing the output of the determined care team assignments, recommendations for care team assignments (including recommended care team compositions by role or individual based on previous outcomes), care contribution curves for an individual patient; providing instructions or outputs of other actions described herein; and logging and/or receiving other feedback from the user/caregiver, in some embodiments. Interface 142 also may be used for providing diagnostic services or evaluation of the performance of various embodiments. Example embodiments of a user/clinician interface 142 and decision support application 140 actually reduced to practice is illustratively provided in FIGS. 6A-6G, which is further described below.

Example operating environment 100 further includes computer system 120 that may take the form of one or more servers and that is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, aspects of decision support application 140 or user/clinician interface 142 may operate on or utilize computer system 120. Similarly, a portion of computing system 120 may be embodied on user/clinician interface 142, application 140, and/or EHR system 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as 122, 124, 126, and 128. Some embodiments of operating system 129 comprise a distributed adaptive agent operating system. Embodiments of services 122, 124, 126, and 128 may run as local services or may be distributed across one or more components of operating environment 100, in the cloud, on one or more personal computers or servers such as computer system 120, and/or a computing device running interface 142 or application 140. In some embodiments, interface 142 and/or application 140 operate in conjunction with software stack 125.

In embodiments, model variables indexing service 122 and records/documents ETL service 124 provide services that facilitate retrieving actions performed for a patient that are electronically recorded in the patient's EHR. Services 122 and/or 124 may also provide services for retrieving and extracting patient physiological variables, and action indicators, which may include frequent itemsets; extracting database records; and cleaning the values of variables in records. For example, services 122 and/or 124 may perform functions for synonymic discovery, indexing or mapping variables in records, or mapping disparate health systems' ontologies. In some embodiments, these services may invoke computation services 126.

Computation services 126 may perform statistical or computing operations such as computing functions or routines for determining decay rates or curves, as further described herein. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing one or more models, including logistic models, for determining the care contribution scores and the appropriate care team assignments, such as the models described in connection to FIGS. 2-3. In some embodiments, computation services 126 use EHR system(s) 160, model data and model storage services 128, and/or other components of example operating environment 100, and may also include services to facilitate receiving and/or pre-processing data. Model data and model storage services 128 may be utilized to perform services for facilitating storage, retrieval, and implementation of the models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more stream processing service(s) (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services in parallel, serially, or operating independently. Some embodiments of the invention also may be used in conjunction with Cerner Millennium®, Cerner CareAware® (including CareAware iBus®), Cerner CareCompass®, or similar products and services.

Example operating environment 100 also includes storage 121 (also referred to herein as data store 121), which in some embodiments includes patient data for a patient (or information for multiple patients), including raw and processed patient data; variables associated with patient recommendations; and information pertaining to clinicians and staff, including healthcare provider policies and shift schedules. Data store 121 may further include recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information, including data and computer-usable instructions; patient-derived data; and healthcare provider information, for example. It is contemplated that the term "data" includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
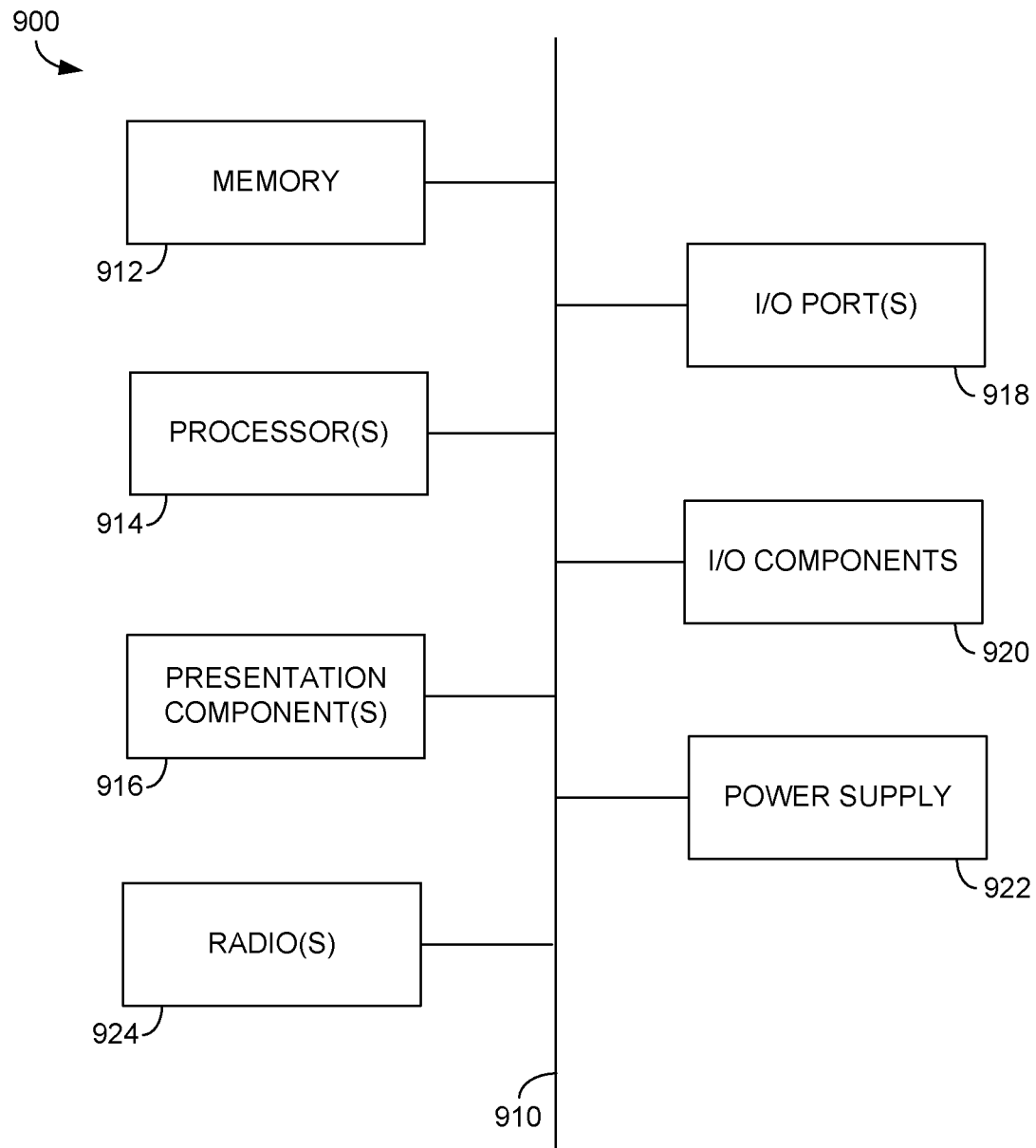

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. Presentation component(s) 916 present data indications to a user or other device. Exemplary presentation components include a display device, speaker, printing component, vibrating component, etc.

In some embodiments, computing system 924 comprises radio(s) 924 that facilitates communication with a wireless-telecommunications network. Illustrative wireless telecommunications technologies include CDMA, GPRS, TDMA, GSM, and the like. Radio 924 may additionally or alternatively facilitate other types of wireless communications including Wi-Fi, WiMAX, LTE, or other VoIP communications. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
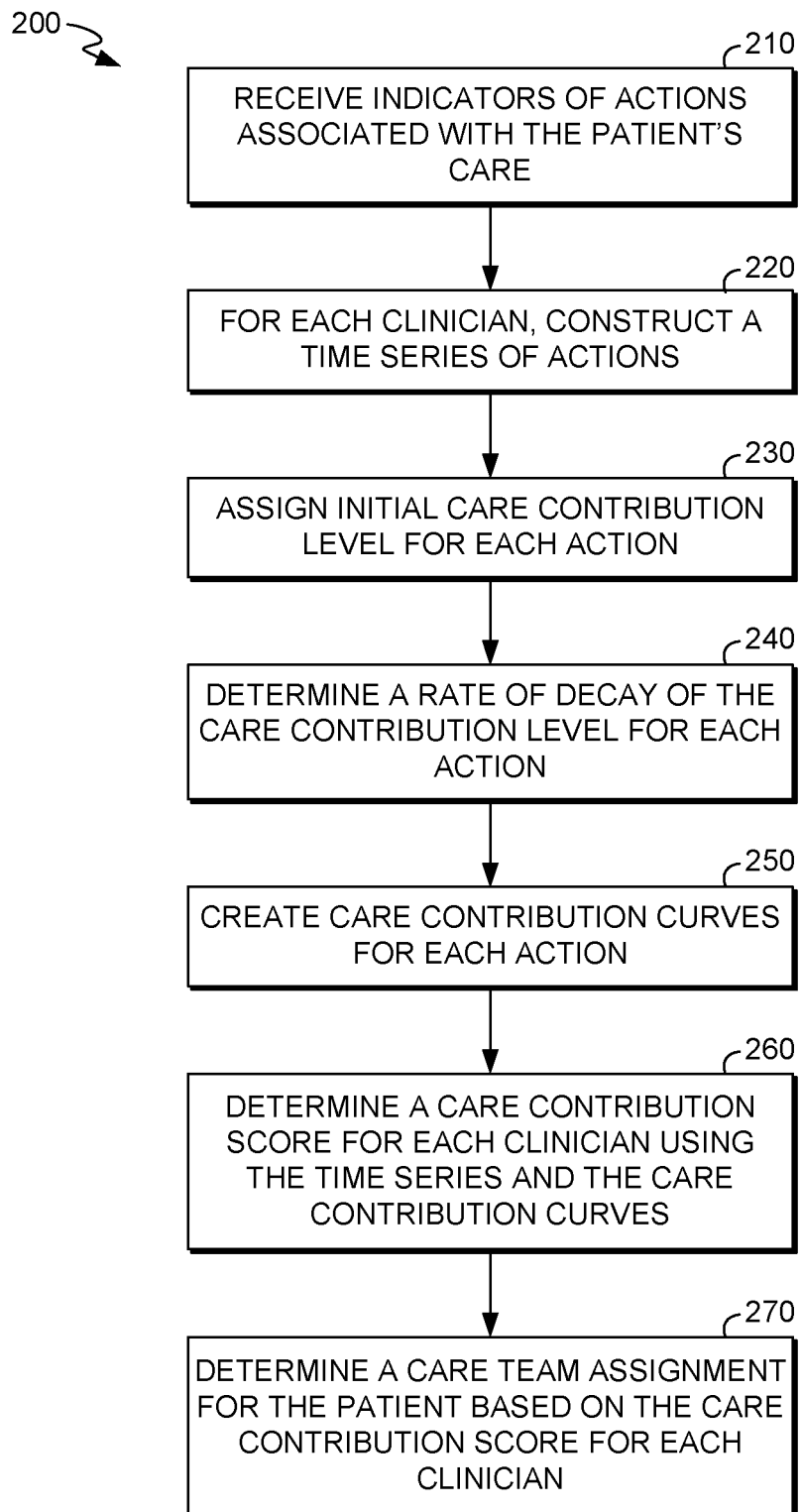
FIG. 2 depicts a flow diagram of a method for providing a decision support system for assigning members to a patient's care team, in accordance with an embodiment of the disclosure.

Turning now to FIG. 2, one example embodiment of a method for generating a care team assignment is provided and is referred to generally as method 200. In particular, example method 200 utilizes the time series of actions taken by a clinician for a patient to determine a care contribution score for each clinician and creates a patient's care team based on the care contribution scores. This method provides an accurate representation of what a care team should be based on clinicians' interactions with the patient by assigning clinicians who actually contribute to the patient's care in a more substantial way compared to other clinicians. In some embodiments, method 200 is suitable for implementation as a computer-performed decision support tool or application for assigning care team members and, thus, providing care team assignment that are more updated and accurately reflect the responsible clinicians compared to conventional technology.

In accordance with method 200, at step 210, a plurality of indications of actions associated with the patient's care is received. Each action is a clinician's interaction relating to the patient's care. In some embodiments, the action may include one of a chart, an order, a clinical event, or a diagnosis. A "chart" action may refer to accessing or reviewing the patient's EHR. An "order" action may include placing an order for the patient, such as an order for a laboratory test or medication. A "clinical event" action may include performing a laboratory test, administering medication, performing an examination, the like. A "diagnosis" action may include entering or updating a diagnosis in the patient's chart. These example actions are not intended to be limiting as it is contemplated that other interactions with the patient, either directly or indirectly, may be performed and received in accordance with aspects of this invention.

During the span of a patient's encounter, such as a patient's hospital stay or portion thereof, such as a 12-hour shift, there may be several actions that are performed or initiated by different clinicians, and an indicator of each action may be acquired in accordance step 210. As the actions may occur at different times and be initiated or performed by different clinicians, each indicator may include a time the action was taken and at least one clinician associated with each action.

The indicators of each action are received from the patient's EHR, such as a medical EHR within EHR system 160 in FIG. 1, or other data storage, or may be received directly from a device being used to perform the interaction.

In some embodiments, the actions for which indicators are received either relate to the patient's EHR, such as reviewing an EHR or updating a diagnosis, or are often performed using an electronic system, such as ordering tests or medications. Accordingly, indicators of these actions may be received from the patient's EHR or the other electronic healthcare systems used by the healthcare provider in the normal course of the patient's care. In other words, the clinicians do not need to perform additional steps for these actions but, rather, embodiments of the disclosure leverage information that is already available to track the patient's interactions. Embodiments of step 210 may acquire the action indictors continuously, periodically, or at non-regular intervals. In exemplary embodiments, the action indicators are received in real time or substantially real time.

At step 220, a time series of the actions is constructed for each clinician associated with the actions. Each time series indicates when a clinician takes an action over a period of time. In some instances, the period of time may be a discrete encounter, such as a clinic visit or hospital admission, or may span longer time periods.

At step 230, a pre-determined, initial care contribution level may be assigned for each action. The care contribution level is an indication of the level of care a clinician has provided to a patient and reflects the amount of involvement and responsibility the clinician has. For example, in some aspects, a clinician's care contribution level is between 1 and 0, with 1 being the highest amount of care contribution and 0 being the lowest amount of care contribution. In exemplary embodiments, the initial care contribution level is the same for each type of action. For instance, each time a clinician performs an action, the care contribution level for the clinician may be set at the maximum care contribution level, such as 1. It is contemplated that, in other aspects, the initial care contribution level depends on the type of action being taken. For example, actions that require more time or attention from a clinician or that carry a greater responsibility, such as ordering a medication, may provide a higher initial care contribution level compared to actions requiring less time or carry less responsibility, such as viewing a patient's EHR.

The care contribution levels may change or decay over time, reflecting the natural decrease in the action's relevance as the action becomes further removed in time. Accordingly, at step 240 of method 200, a rate of decay of the care contribution level for each action associated with the clinician is determined. In some embodiments, for instance, an action may trigger a clinician's care contribution level to be set at 1, and the clinician's care contribution level may decrease to 0 if there are no subsequent actions associated with the clinician for that patient prior to reaching a care contribution level of 0.

In exemplary aspects, the rate of decay depends both on the clinician's role and the type of action performed. Role-action pairs may be grouped into tiers as shown in Table 1 below.

TABLE 1

Example Parameters for Care Contribution Curves

| Tier (Γ) | Alpha (α) | Beta (β) | Role-Action |
|---|---|---|---|
| 1 | 0.5 | 0.5 | Any-Chart |
| 2 | 1 | 3 | Any-Diagnosis |
| 3 | 3 | 5 | Nurse-Event |
|   |   |   | Other-Event |
| 4 | 5 | 7 | Physician-Event |

TABLE 1-continued

Example Parameters for Care Contribution Curves

| Tier (Γ) | Alpha (α) | Beta (β) | Role-Action |
|---|---|---|---|
|   |   |   | Resident-Event |
|   |   |   | NP-Event |
|   |   |   | PA-Event |
|   |   |   | Nurse-Order |
|   |   |   | Other-Order |
| 5 | 8 | 8 | Physician-Order |
|   |   |   | Resident-Order |
|   |   |   | PA-Order |
|   |   |   | NP-Order |

The tiers may be based on a determination of which role-action pairs should have the longest-lasting effect on a care contribution level based on the amount of responsibility and involvement typically associated with the role-action pair. For instance, in embodiments utilizing the tiers in Table 1, the levels of responsibility and involvement afforded to the different actions follows this progression: chart<diagnosis<event<order. Additionally, physicians, residents, physician assistants (PA), and nurse practitioners (NP) may have greater responsibility and, therefore, are in higher tiers compared to nurses and other clinicians. In some aspects, physicians, residents, physician assistants and nurse practitioners are considered to belong to a "physician" role type and nurses and other clinicians are considered to belong to a "non-physicians" role type.

Based on the tier, a rate of decay may be determined using the corresponding alpha (α) and beta (β). Alpha indicates the time until the care contribution level begins to decay and beta indicates the duration over which the contributions decay. In some embodiments, the rate of decay is determined using a logistic function to produce a logistic curve, also referred to herein as a care contribution curve. For example, the logistic function used may be:

$$f(t; t_\alpha; \alpha; \beta) = \frac{1}{1 + e^{[k(\beta)*(t-t_0(t_\alpha, \alpha, \beta))]}}$$

where t is the time since the patient's encounter begun; $t_\alpha$ is the time since the patient's encounter begun that the action occurs; α is the time until the care ratio begins to decay and β is the duration over which the care ratio decays. In exemplary aspects, the units for time and durations are in hours. Using tier 4 as an example, if αΓ=5 and βΓ=7, the care contribution will decay below some tolerance ε after 12 hours. The functions k and $t_0$ that allow for these interpretations of α and β are:

$$k(\beta) = \frac{\log 99}{\beta}$$

$$t_0(t_\alpha, \alpha, \beta) = t_\alpha + \alpha + \frac{\beta}{2}$$

Using the rates of decay and the initial care contribution levels, at step 250, care contribution curves may be generated for each action. Care contribution curves illustrate the change(s) in a clinician's care contribution level for a particular patient over a period of time, with the changes being determined from the rates of decay. In an example embodiment actually reduced to practice, a tolerance of ε=0.01 was found to have worked well and provided the example care contribution curves depicted in FIG. 3.

Figure 3:
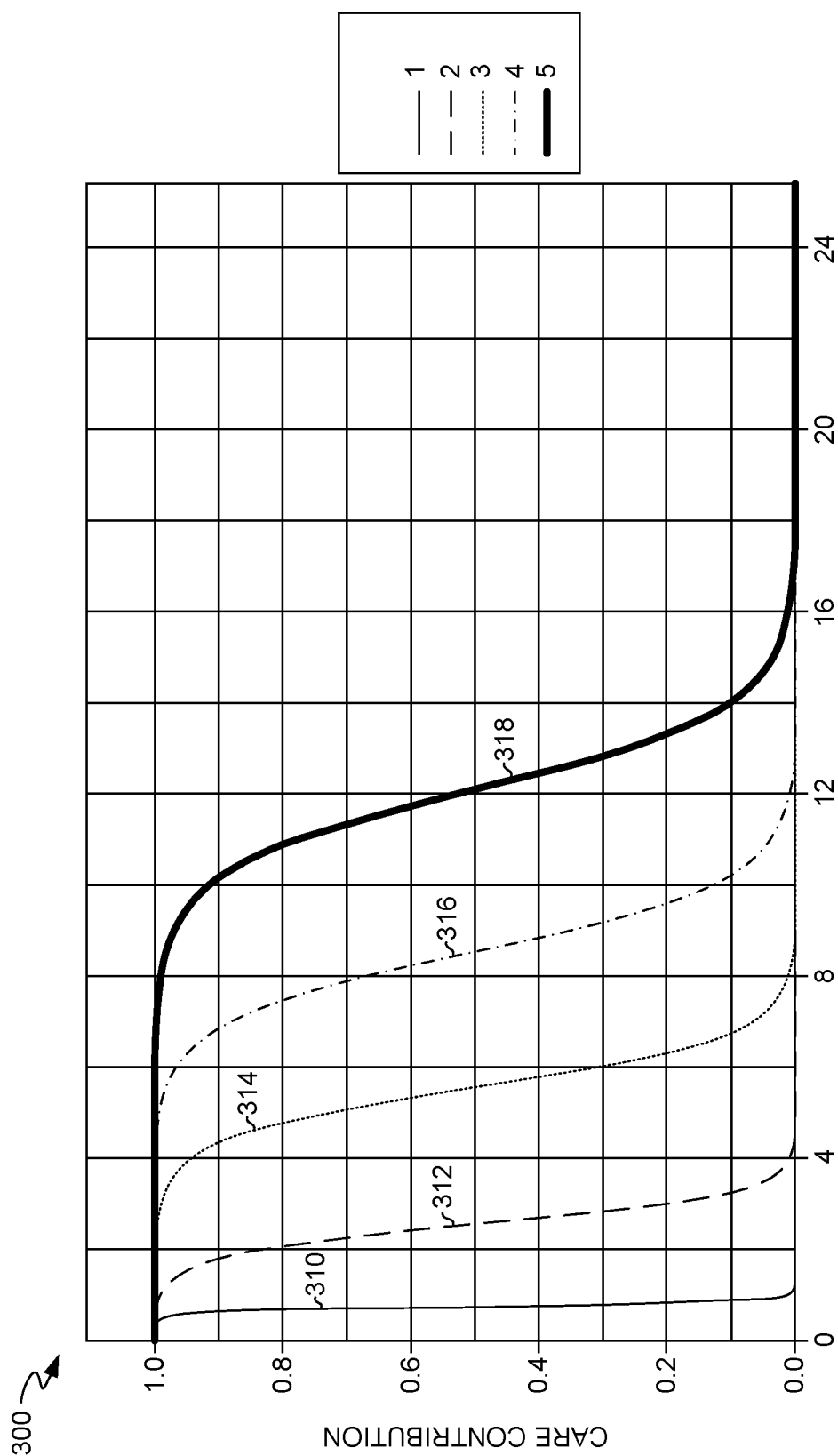
FIG. 3 depicts care contribution curves for each tier based on a type of action and role of the clinician, in accordance with an embodiment of the disclosure.

FIG. 3 provides a graphical representation 300 of the care contribution curves 310, 312, 314, 316, and 318 that are each corresponds to a tier in Table 1. Each curve is based on an action occurring at t=0. The care contribution level for each curve begins to decay at different times and, once decay begins, decays at different rates. The tier 1 curve 310, which may represent a nurse viewing a patient's chart, begins to decay relatively soon after the action occurs and decays at the quickest rate. The tier 5 curve 318, which may represent a physician placing an order for a patient, does not decay until approximately 8 hours after the order was placed and takes the longest time to decay to 0 once decay begins.

The role-action pairs used to determine the tier and rate of decay may not perfectly match with the roles and actions provided in the indicators of the action. For instance, the indicator may indicate that the action taken was administering a medication, and embodiments of the disclosure categorize that action into a "clinical event" action type. Additionally, the clinician role may be initially indicated as being a cardiologist, and embodiments categorize that role into a "physician" role type, or a clinician role may be a respiratory therapist and embodiments may categorize that clinician as a "non-physician" clinician role.

Figure 4:
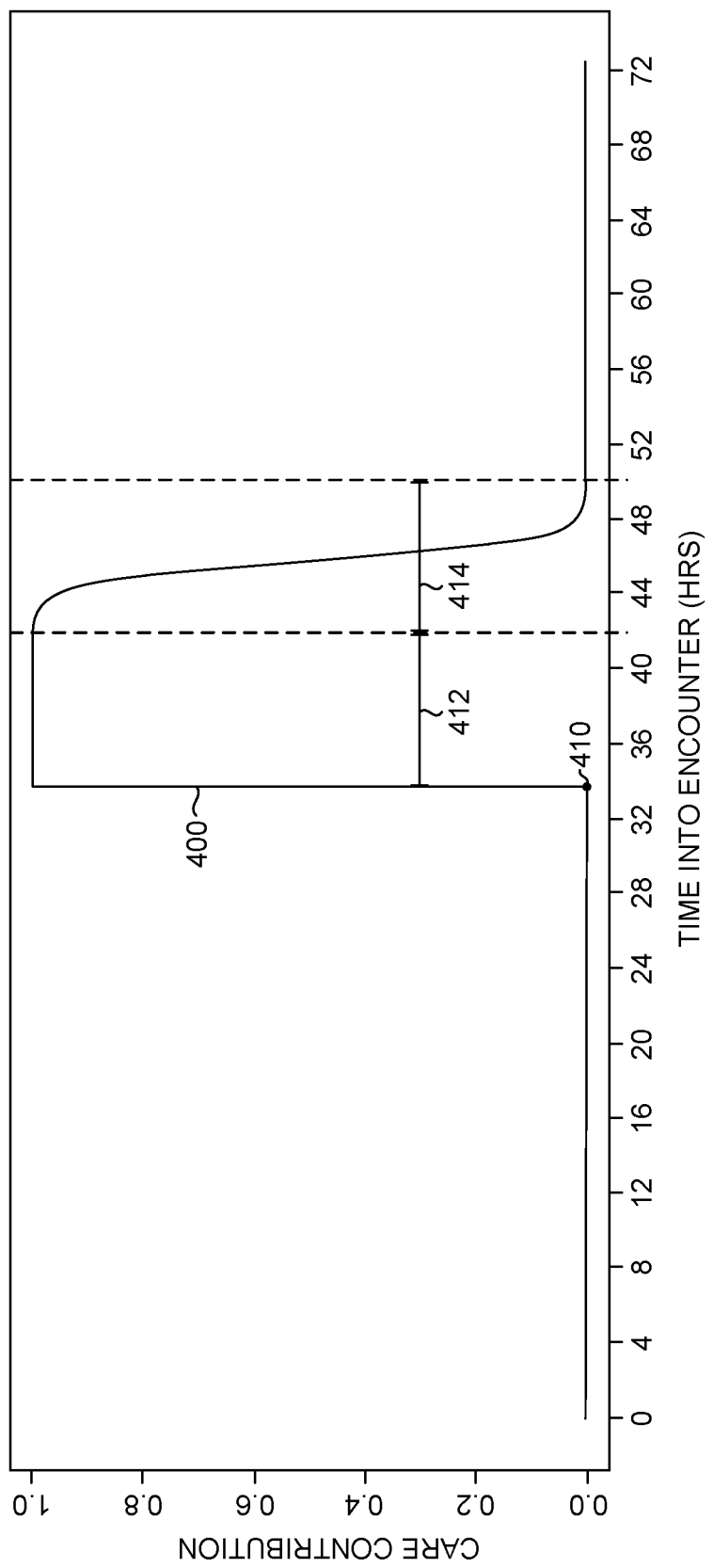
FIG. 4 depicts a care contribution curve for a clinician based on a single action, in accordance with an embodiment of the disclosure.

FIG. 4 illustrates an example clinician's care contribution curve 400 for a patient's encounter in which the clinician took one action. For example, the care contribution curve 400 may be associated with a nurse practitioner who placed an order for the patient. As shown in FIG. 4, the clinician took the action approximately 34 hours into a patient's encounter. Accordingly, the action time 410 (also referred to herein as the interaction time) is the time associated with the action. In some aspects, the action time 410 is the time that an action is electronically logged. For instance, when a clinician views a patient's EHR or completes an electronic order for the patient, the action will be logged at that time, and the log time may be automatically associated with the action and used for the action time 410. In some aspects, a clinical event, such as administering a test, is captured as an action when documentation relating to the action is added to the patient's EHR, and the action time is the time the documentation for the clinical event is added. The action time may also be entered or adjusted manually by a user. As an example, if a clinician performs an exam on the patient without access to the patient's EHR, the clinician-user may later chart that an exam occurred, including recording the time that the exam occurred.

Following the care interaction curve 400, at the action time 410, the clinician's care contribution level is set to 1 and then decays back to 0 over time. In this example, the period of time 412 before the care contribution begins to decay (or alpha) is approximately eight hours, and the duration of the decay 414 (or beta) is approximately eight hours, such that the clinician's care contribution level is back to zero 16 hours after the action time 410.

Figure 5:
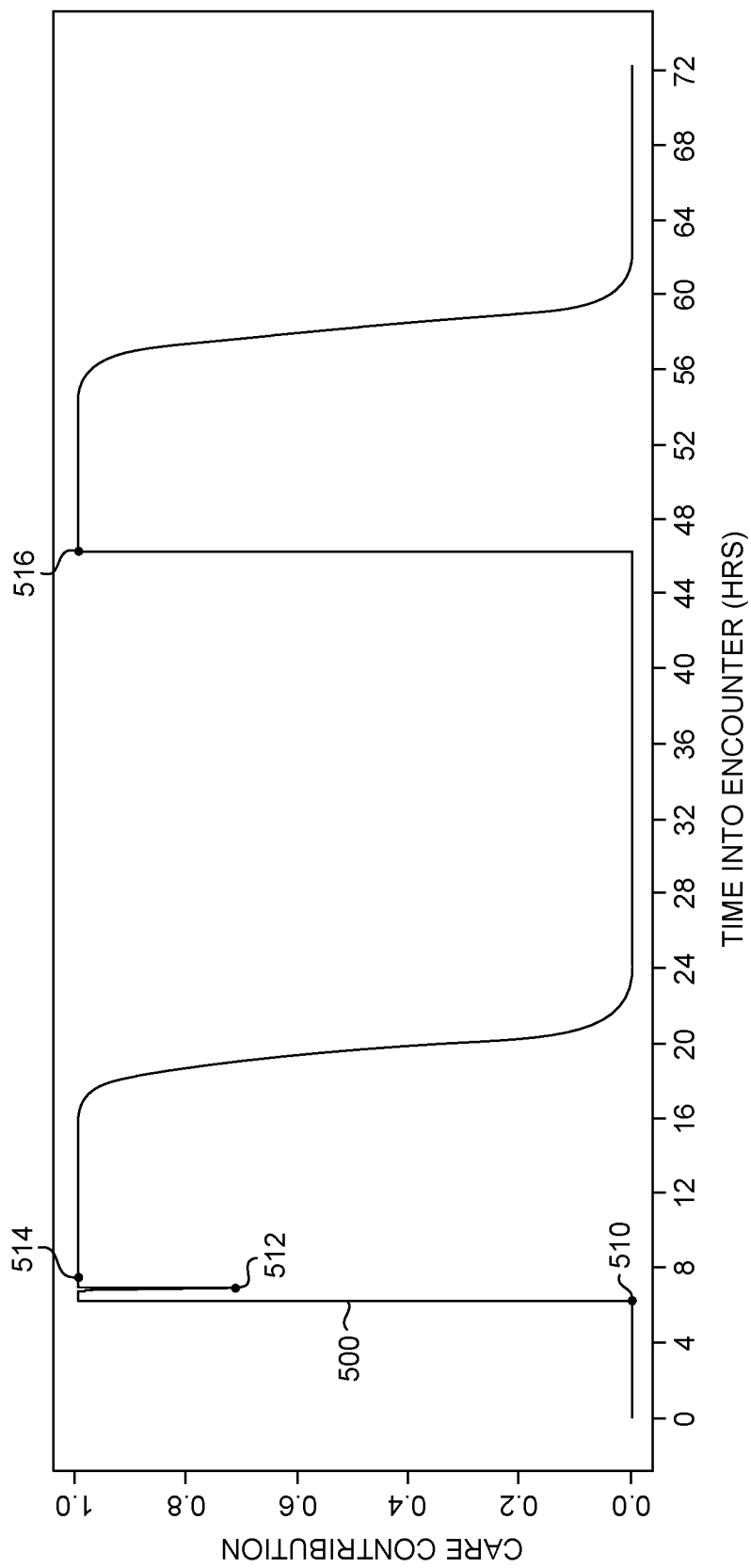
FIG. 5 depicts a care contribution curve for a clinician based on multiple actions, in accordance with an embodiment of the disclosure.

When a clinician takes multiple actions for a patient, each action re-sets the care contribution level to the initial contribution level (such as the maximum contribution level of 1), and the curve begins to decay until it either reaches 0 or another action occurs. FIG. 5 depicts a care contribution curve 500 of a clinician who had multiple interactions with the patient. In this example, the clinician, who may be a physician, took at action, such as viewing the patient's chart, approximately 6 hours after the patient's encounter began, as shown by the jump in the care contribution level at action time 510. Before the care contribution level from the first action decays to 0, additional actions occur that each raise the care contribution level back to 1. For example, approximately 40 minutes after the first action, at time 512, a second action, such as viewing the chart again, may occur. Although the care contribution level for the action at time 510 had not yet decayed, the care contribution level is reset at 1, and a new rate of decay is determined. Approximately, thirty-five minutes later, at time 514, another action occurs that maintains the care contribution level to 1, and a new rate of decay is determined. After the care contribution level decays to and remains at 0 for some time, another action is taken at time 516, which may be approximately 46 hours into the patient's encounter. At this time, the physician-clinician may have viewed the patient's chart and placed an order, which triggers the care contribution level to be set at 1 again.

In exemplary aspects, when there are simultaneous or near simultaneous actions or overlapping curves from subsequent actions, the maximum curve may be utilized. For instance, at time 516, there may be an order action and a chart action, which have different rates of decay. Although there are multiple actions, the care contribution level is reset only once at that time 516 just as it would for a single action being taken. However, the longest decay rate amongst the different interactions may be used so that the maximum curve is generated. For instance, for the order and chart actions taken at time 516, either the tier 1 or tier 5 decay rate may apply. Because the decay rate for tier 5 is longer than the rate for tier 1, the curve would be greater using the tier 5 rate and, therefore, the tier 5 rate is chosen. In embodiments, the number of simultaneous actions taken at a time does not change this process. For instance, at time 514, the physician-clinician may have placed seven orders, such as orders for laboratory testing or medications, and entered two diagnoses. Although there are multiple actions, the care contribution level is reset only once at that time, and the decay rate for order actions is used.

Similarly, when the contribution level for an action does not fully decay due to a subsequent action re-setting the contribution level to the maximum level, the maximum curve of the two actions will be used. For instance, a physician may place an order, which decays at the slowest rate, and then later review the patient's chart, which has a more rapid decay rate, before the order action decays. If continuing with decay from the initial order action would provide greater area under the curve than resetting the care level for the chart action, the decay from the order action and resulting curve are used.

Although FIGS. 3-5 illustrate logistic curves with the decay being from 1 to 0, it is contemplated that different functions producing different types of curves capable of decaying to 0 may be used. In other embodiments, the curve may be a linear curve, a step-function curve, or a Heaviside function curve in which the curve immediately drops off at a point in time. A Heaviside function curve may be used, for example, when there is a shift change such that a clinician's care contribution level instantly drops to 0 when a shift change occurs and the clinician is no longer available to help the patient. In some aspects, multiple functions may be used for different clinicians or may be used in conjunction with one another for the same clinician.

Returning to method 200, once rates of decay are determined and care contribution curves generated, method 200 includes determining a care contribution score for each clinician, at step 260. The care contribution score may comprise a composite or overall care contribution level and be determined using the times series and the care contribution curves. In exemplary embodiments, the care contribution score may be referred to as the normalized care contribution and comprises the area under the care contribution curve (AUC) divided by the relevant period of time, such as the patient's encounter. In the examples in FIGS. 4-5, the patient's encounter of 72 hours is likely the patient's entire admission into a hospital. The patient encounter may also be shorter durations such as a patient's visit to a clinic or physician's office or a 12-hour hospital shift. Or, the encounter may be a longer period of time. Longer periods of time may be used when a patient's care team is being determined for long-term care situations or in-home care. As an example, for an obstetrics care team, the "encounter" or relevant period of time may be the entire pregnancy or may be the time periods between check-ups.

Because the care contribution curve is a function of a period of time, method 200 may include receiving a time or time frame. For example, the method may comprise receiving the current time and determining the period of time to be the time from the start of the patient's encounter to the current time. In other aspects, the period of time may be a pre-determined amount, such as the previous 12 hours or 72 hours from the current time, or may be selected by the user. In other aspects, the time or time frame received may be a previous time. For instance, a user may be interested in learning what the care team assignment should have been at a previous point in time, such as the day before. In that case, the time received may be a past time, and the relevant period of time used to calculate the care contribution score is a period of time looking back starting with the past time.

For example, in FIG. 4, the AUC for the care contribution curve 400 may be divided by the period of 72 hours such that the nurse practitioner performing the action for this example may be determined to have a care contribution score of 0.166. Based on the curve 500 in FIG. 5, the physician may be determined to have a care contribution score of 0.35, which accounts for the multiple interactions.

At step 270, a care team assignment for the patient may be created based on the care contribution score for each clinician. The care team assignment may comprise a group of one or more clinicians responsible for the patient's care. The care team may include clinicians with different roles or role-specialty combinations. For instance, the care team may include only one physician clinician from each specialty represented by the patient's potential care team members and/or may have only one nurse. In exemplary aspects, the care team assignment may be determined by comparing care contribution scores for clinicians having a role or role-specialty combination in common and ranking the clinicians with the highest relative contribution scores above other clinicians with that same role and specialty. The highest-ranked clinician in each role (or role-specialty combination) may be assigned to the patient's care team. In some aspects, only certain roles or role-specialty combinations are used for the care teams, and, as such, certain clinicians may be disregarded as potential care team members based on their role and specialty, regardless of the clinicians' contribution scores. The roles and/or role-specialty combination used for a patient may be dependent on the healthcare facility or the patient's condition.

Further, assigning care team members may also comprise comparing the care contribution scores to a threshold score and determining that the clinician's score satisfies the threshold. Specifically, in some embodiments, the care contribution score must meet or exceed a minimum threshold in order for the clinician to be considered part of the care team, even if that there were no other potential team members with the same role and, in some aspects, specialty. The threshold may be pre-determined or may be context dependent. In an example embodiment, a pre-determined threshold score of 0.05 is used, and clinicians with care contribution scores less than 0.05 are not considered for the care team assignment.

For clinicians who do not have the highest care contribution score for the clinician's role and specialty, some embodiments may include providing suggested alternative care team members. These suggested alternatives may be utilized when the primary care team member with the same role and specialty is not available such as, for example, when the primary care team member's shift is over or when the primary member will be detained with another patient for an extended period of time. In some aspects, the slots for the primary care team members may be auto-populated with the clinicians having the highest score in the respective role-specialty, and alternative members may be communicated to the user with the ability to manually override any assignment to replace a primary care team member with a suggested alternative or other clinician. In some aspects, the clinician's care contribution score must satisfy a threshold score before being considered as an alternative care team member.

FIGS. 6A-6G depict graphical representations of the care contributions of potential care team members from an example embodiment actually reduced to practice. Specifically, FIGS. 6A-6G represent a patient's admission to the hospital for approximately 72 hours (i.e., an encounter), during which the patient interacted with several clinicians, including two oncologists, two cardiologists, one emergency department physician, and one nurse practitioner. Determining the appropriate composition for the clinical care team involves determining and ranking the care contribution scores for each potential care team member based on the member's interactions with the patient. Because the care team may include one clinician for each role and, in some instances, specialty, the patient's care team may comprise one oncologist, one cardiologist, one emergency department physician, and one nurse practitioner. Because the patient had interactions with only on emergency department physician and one nurse practitioner, both the emergency department physician and the nurse practitioner who interacted with the patient may be automatically included on the care team. In some aspects, the care contribution scores for the emergency department physician and the nurse practitioner may be determined and compared to a minimum threshold to determine whether either of these clinicians may be assigned to the patient's care team.

Figure 6A:
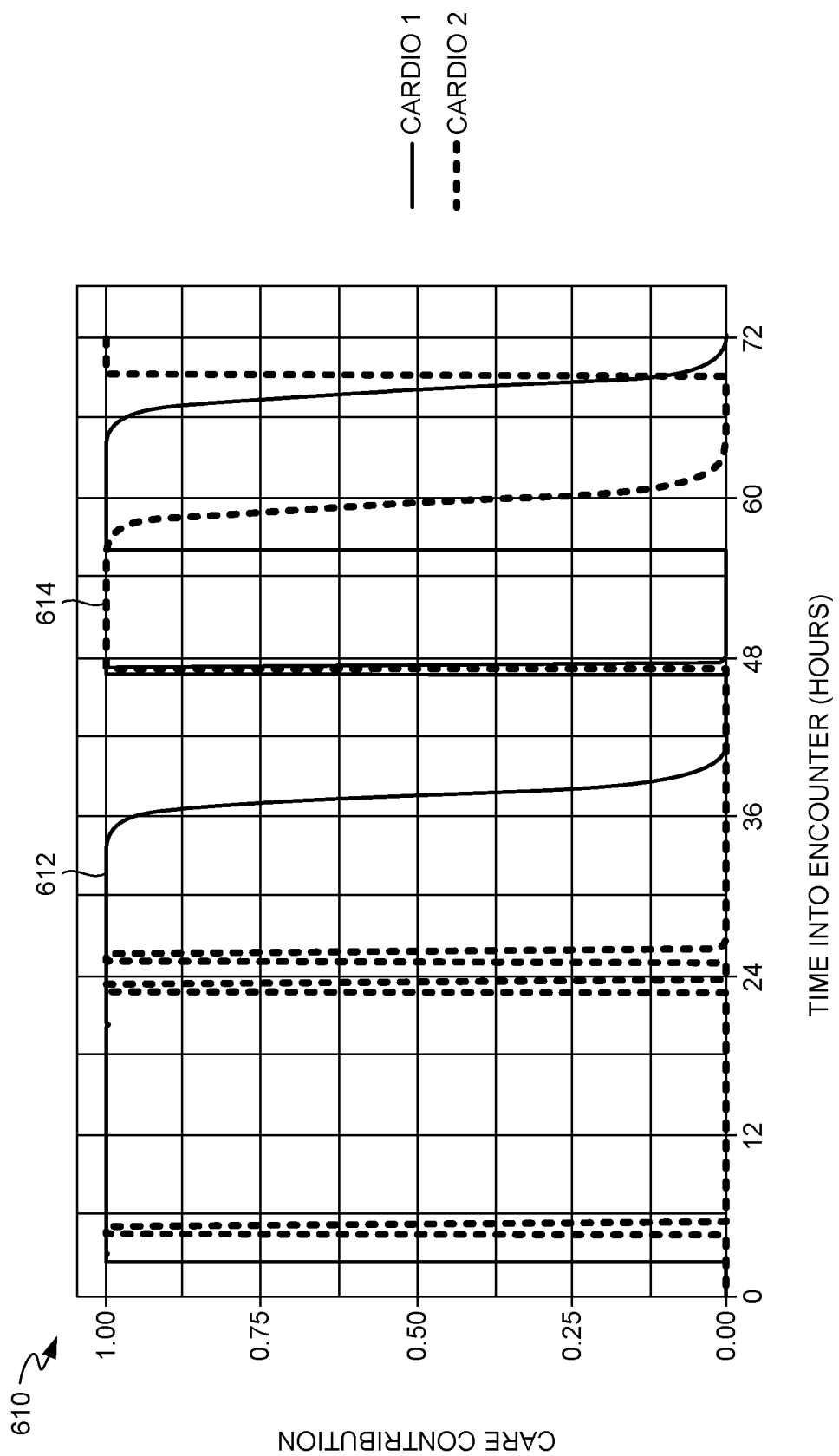
FIG. 6A depicts care contribution curves for two clinicians with a common role and specialty, in accordance with an embodiment of the disclosure.

For the oncologists and the cardiologists, the care contribution scores are determined and used to rank each physician within the respective specialty to determine the most appropriate clinicians for the patient's care team. FIG. 6A depicts a composite care contribution curves for the time series 610 for both cardiologists who interacted with the patient. Actions with associated time stamps are received for each cardiologist. Rates of decay for each action are used with the time-stamped actions to generate care contribution curve 612 for cardiologist 1 and care contribution curve 614 for cardiologist 2. As indicated by curve 612, cardiologist 1 first interacted with the patient approximately 2 hours into the patient's encounter and ordered some testing for the patient, which set cardiologist 1's care contribution level at 1. Over the next several hours, cardiologist 1 checked on the patient multiple times and ordered additional testing or medications at different times. Each time a new action occurs, an initial care contribution level for the action is the maximum care contribution level, which is 1 and, therefore, the curve 612 is reset at 1. Accordingly, between t=20 and t=34, the declines in the care contribution level are barely perceivable or not perceivable because cardiologist 1 had interactions before the relevance of the previous action began to decay at all or to a noticeable extent. Approximately 26 hours into the patient's encounter, cardiologist 1 ordered additional testing, and the care contribution level decayed to 0 before another action occurred. At approximately 47 hours into the interaction, cardiologist 1 checked in on the patient again, which involved viewing the patient's chart, and then ordered medication approximately 9 hours later. Cardiologist 1's care contribution level decreased to 0 by the time the patient was discharged after 72 hours.

During the first 48 hours of the patient's encounter, cardiologist 2 may have viewed the patient's chart a few times, resulting in the three spikes in the first portion of cardiologist 2's care contribution curve 614. At approximately 2 hours, cardiologist 2 diagnosed the patient and ordered medication. In accordance with aspects utilizing the tiers in Table 1, the resulting rate of decay is for the medication order, which belongs to a higher tier and, therefore, is associated with a slower decay compared to the diagnosis action. At 70 hours, cardiologist 2 ordered additional medication for the patient, resulting in another jump to a level of 1, and cardiologist 2's care contribution level did not have a chance to decay to 0 before the patient's was discharged and the encounter ended.

Over the entire 72-hour encounter, cardiologist 1 has a normalized care contribution score of 0.663, and cardiologist 2 has a normalized care contribution score of 0.248. Accordingly, in some aspects in which the entire 72-hour encounter, which may be the patient's hospital admission, is used as the relevant time period, cardiologist 1 may be selected for the care team as the responsible physician in cardiology. In other aspects, only a portion of the hospital admission may be used for determining the care contribution score and, consequently, care team assignments. For instance, in embodiments in which only the previous hour is used as the encounter length and where the care team assignment is created at t=60, embodiments of the disclosure may assign cardiologist 2 because, during that particular period, cardiologist 2 has the higher care contribution level.

Further, as illustrated by FIG. 6A, the contribution levels change due to decay or additional actions occur and, as such, the clinicians with the highest care contribution score may change as a patient's encounter progresses. For instance, using the encounter in FIG. 6A, an initial care team may be assigned at t=12, and cardiologist 1 may be assigned to the team over cardiologist 2. However, if using as 12-hour shift as the relevant time period for calculating the care contribution score, at t=60, cardiologist 2 may now have a higher care contribution score than cardiologist 1. As such, the care team may be updated so that cardiologist 1 is removed and cardiologist 2 is added. These updates to care team assignments may occur in real time.

Figure 6B:
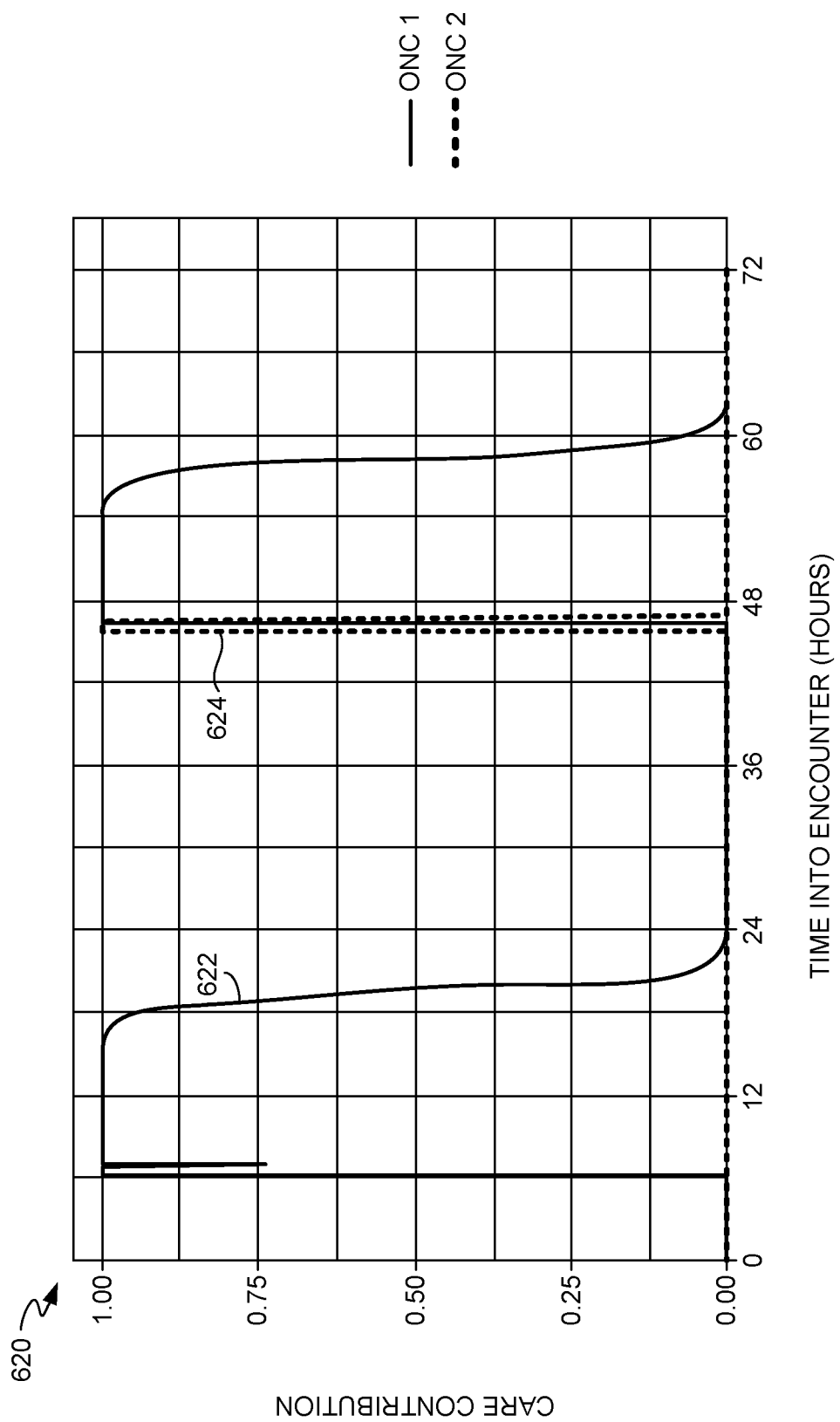
FIG. 6B depicts care contribution curves for two clinicians with a common role and specialty, in accordance with an embodiment of the disclosure.

Similar to FIG. 6A, FIG. 6B depicts composite care contribution curves 620 for both oncologists who interacted with the patient. Actions with associated time stamps are received for each oncologist, and rates of decay are used with the time-stamped actions to generate care contribution curve 622 for oncologist 1 and care contribution curve 624 for oncologist 2. As indicated by curve 622, oncologist 1 first interacted with the patient about 6 hours into the patient's encounter and consulted with the patient, which included viewing the patient's EHR. Because viewing a patient's EHR is a tier 1, the care contribution level began to decay rapidly; however, before the care contribution level decayed to 0, oncologist 1 ordered additional testing, causing the care contribution level to be re-set at 1. Curve 622 dropped to 0 at about 23 hours into the encounter. After 46 hours into the encounter, oncologist 1 ordered additional testing, which caused another increase to a care contribution level of 1. During this time, oncologist 2 had only one interaction with the patient, resulting in the spike in curve 624 at about t=46. Using area under the curve over the encounter period as the care contribution score, oncologist 1 had a care contribution score of 0.350, and oncologist 2 had a care contribution score of 0.010. As such, embodiments of the present disclosure may assign oncologist 1 to the clinical care team.

The patient may have had other interactions with other clinicians. For instance, the patient may have interacted with several nurses, radiologists, pharmacists, respiratory therapists, behavioral therapists, patient care technician, and patient care managers. One individual from each of these other roles and, if applicable, specialty, may be selected for the care team. In other instances, the care team may exclude certain clinician roles, such as patient care technician, from being chosen as a primary care team member, but those roles may be reserved for alternative care team members. In some embodiments, the care team may have a predetermined maximum number of positions within the care team, and certain roles may be included only if other roles, such physicians, physician's assistants, and nurse practitioners, do not fill up the limited number of care team positions.

In accordance with some embodiments of the present disclosure, various graphical illustrations may be created for conveying potential care team members and/or the care team assignment. FIG. 6C, for instance, depicts a table 630 for physicians who are potential care team members, and table 630 may be part of a graphic user interface presented to a user. The table 630 may include rows for each potential care team member and various columns with information pertaining to the clinician and/or the actions taken. For instance, table 630 may include a name column 632 with names of the clinicians and columns 634 and 646 listing the clinician's role and specialty area, respectively. In exemplary aspects, the team member's name is actually provided, but, in the embodiment shown in FIG. 6C, identifying information has been replaced with generic titles. Table 630 may also have column 638 for the care contribution score, which is labeled normalized contribution in FIG. 6C, and several other columns, which are collectively labeled as 650, with information about the actions each clinician took for the patient's care, such as the number of orders, events, chart views, and diagnoses.

Figure 6D:
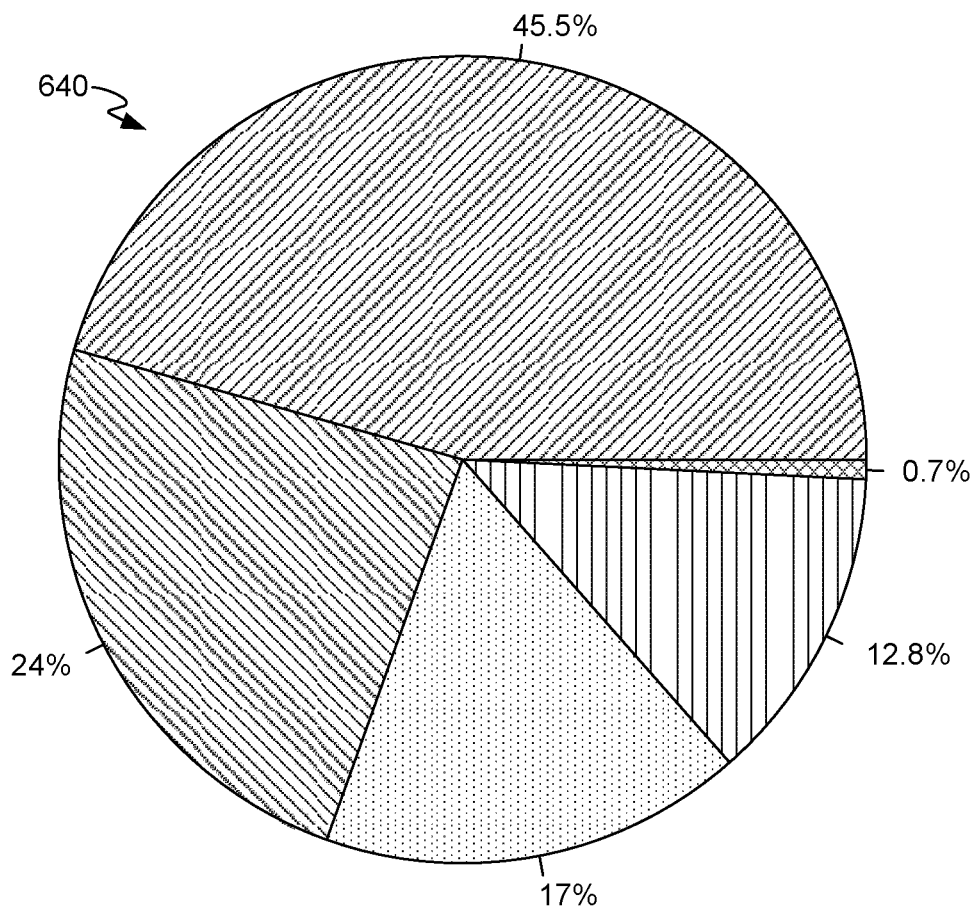

FIG. 6D provides another representation 640 of potential physicians as care team members in the form of a pie cart. Pie chart illustrates the relative contributions to the patient's care from each physician. A user may be provided with a graphic interface with representation 640 to quickly discern the differential levels of contribution to determine appropriate care team assignments, including whether the assignments need to be changed. FIGS. 6C and 6D may be utilized in embodiments presenting recommendations for care team assignments that are ultimately selected by a user or in embodiments in which a user may manually override the automatically assigned care teams. In both cases, the information pertaining to the selected care team members, including their care contribution scores, provided in FIGS. 6C-6D may be helpful in determining which clinicians to select.

Figure 6E:
FIG. 6E-F depict graphical representations of the care contributions for selected care team members, in accordance with an embodiment of the disclosure.
Figure 6F:
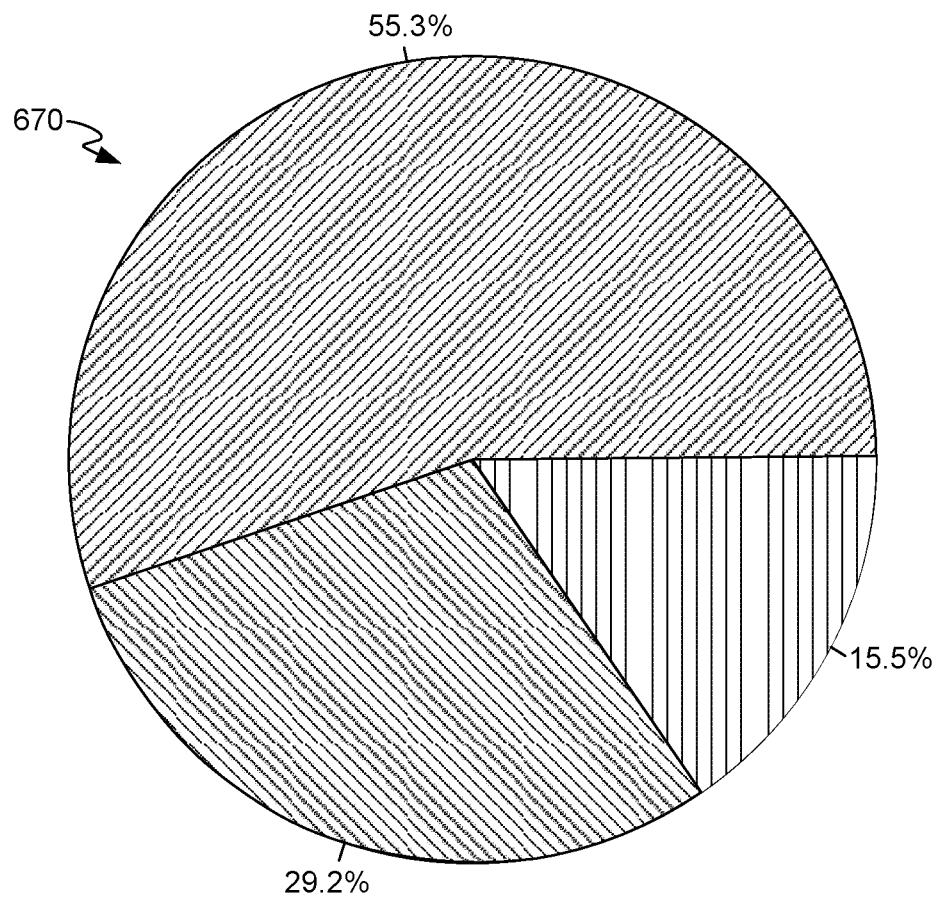

FIGS. 6E and 6F provide graphical representations similar to what was depicted in FIGS. 6C and 6D except that table 660 and pie cart 670 of FIGS. 6E and 6F, respectively, may include only information for the physician-clinicians who are selected as care team members. Accordingly, FIGS.

6E and 6F only represent the care contributions from cardiologist 1, oncologist 1, and emergency department physician.

Figure 6G:
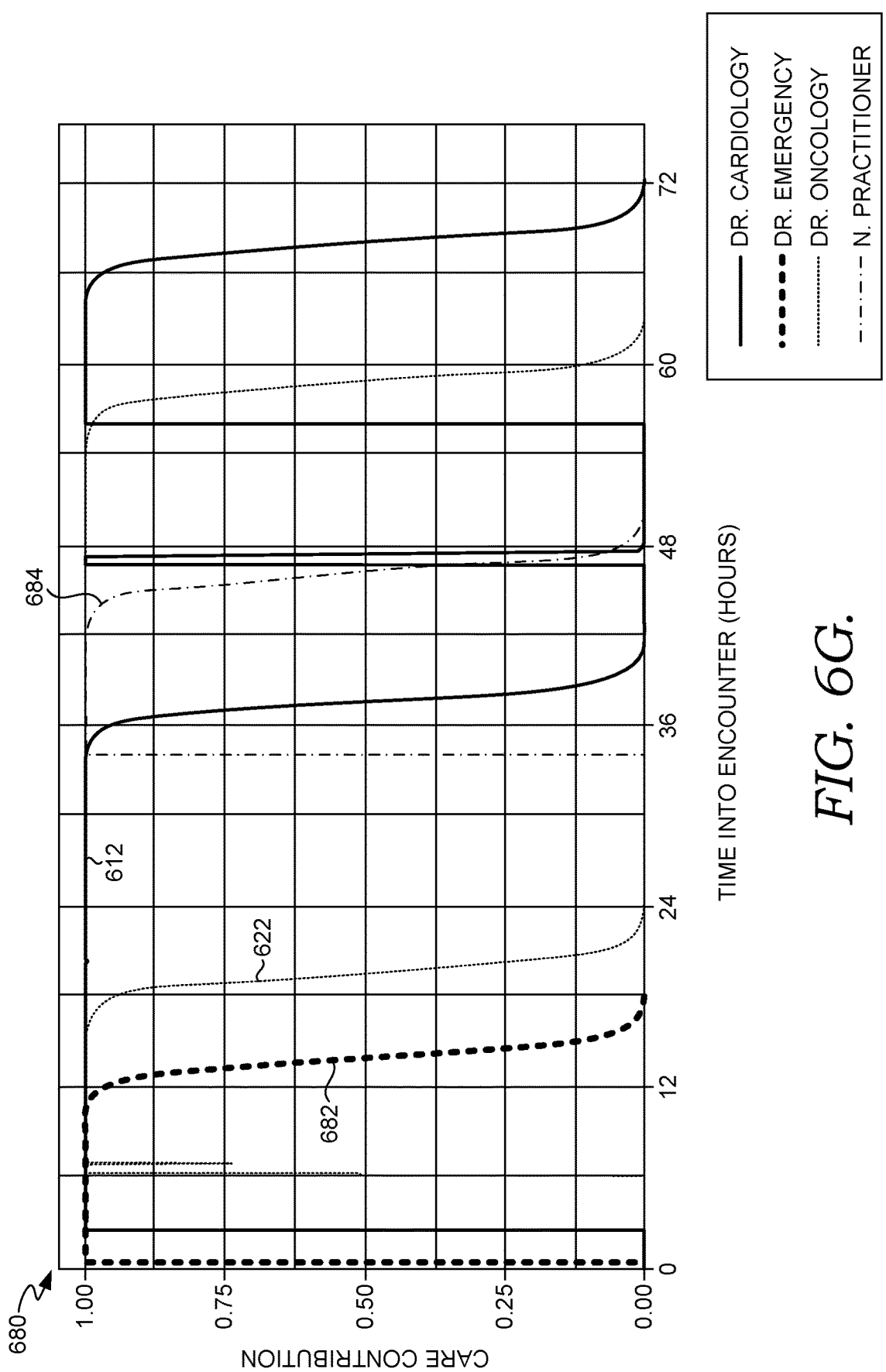
FIG. 6G depicts a composite time series of a patient's encounter for the selected care team members, in accordance with an embodiment of the disclosure.

Additionally, time series with care contribution curves from the entire care team may be created and presented to a user in accordance with aspects herein. FIG. 6G depicts a time series 680 with care contribution curves for the selected care team from the example in FIGS. 6A-6F. As illustrated, the time series includes curve 612 for cardiologist 1, curve 622 for oncologist 1, curve 682 for the emergency department physician, and curve 684 for the nurse practitioner overlapping each other. Time series 680 provides a general overview of the frequency and type of interactions a patient has during his or her encounter and may be presented on a user interface for a provider or patient.

As described, embodiments of the disclosure may track clinicians' interactions with the patient to create a care team assignment that accurately reflects the clinicians' involvement and responsibility with the patient's care. This care team assignment may be created based on an entire encounter such that the assignment may be used to look to who should be held responsible for the encounter, or it may be created and updated on a regular or periodic basis as the patient's encounter progresses so that there is a real-time tracking of the appropriate care team.

In addition to determining responsibility, embodiments of this disclosure may also be directed to evaluating the adequacy of current assignments. For instance, if manual assignments are being used, embodiments may suggest care team assignments and identify discrepancies between the actual assignment and the suggested assignment. These discrepancies may be used to recognize problems in the actual assignment process and/or issues in the care process that result in the discrepancies. In some aspects, embodiments compare the suggested care team assignment to the actual care team assignment and automatically provide a notification to a user, such as the patient's care manager, when a discrepancy is identified. The notification may be provided via a user/clinician interface, such as interface 142, described in connection with FIG. 1A.

Further, embodiments of the disclosure may be used as a learning tool to optimize care team assignments. For instance, embodiments may associate a patient's outcome with the care team assignment and utilize that information to determine optimal care team compositions based on which care team assignments are associated with in better patient outcomes. Optimal care team compositions may include an optimal number of care team members, an optimal combination of roles/specialties on a care team, or individual clinicians who are associated with better outcomes. For instance, if two patients who present with chest pain both see a cardiologist but only one patient sees an oncologist, embodiments may determine whether the patients have different outcomes and, if so, utilize that information with information learned from other interactions to determine whether a combination of both a cardiologist and oncologist for patients with chest pain is better than only a cardiologist. Further, the optimal number or frequency of interactions with a patient or the optimal types of actions, including, in some aspects, the sequence of actions, may be learned based on patient outcomes. Such learning techniques may involve using one or more machine-learning models. Understanding optimal care teams and interactions with the patient may lead to improved results for patients in the future.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Non-transitory computer-readable media having computer-executable instructions embodied thereon that when executed, cause operations to be performed, the operations comprising:
   receiving, in real-time directly from a device used to perform an action, a plurality of electronic indicators of actions associated with the patient's care, each electronic indicator including a time that the action is taken and at least one clinician associated with the action;
   constructing a time series of actions for each clinician associated with the actions;
   assigning an initial care contribution level for each action within the time series for each clinician;
   determining a rate of decay of the care contribution level for each action associated with each clinician;
   creating a care contribution curve for each action based on the initial care contribution level and the rate of decay;
   determining a care contribution score for each clinician using the time series and the care contribution curves; and
   creating a care team assignment for the patient based on the care contribution score for each clinician, the care team assignment being a group of one or more clinicians responsible for the patient's care.

2. The media of claim 1, wherein the rate of decay for each action is based on an action type for the action and a clinician role for the clinician associated with the action.

3. The media of claim 2, wherein the type of action includes one of viewing the patient's chart, placing an order, a clinical event, and diagnosing the patient.

4. The media of claim 2, wherein the role of the clinician is one of a physician and a non-physician.

5. The media of claim 2, wherein the rate of decay includes a period of time after the action that the care contribution begins to decay and a period of time over which the care contribution decays.

6. The media of claim 1, wherein the care contribution level is between 1 and 0, wherein the initial care contribution level assigned to each action is 1.

7. The media of claim 1, wherein the method further comprises receiving a current time.

8. The media of claim 7, wherein the care contribution score comprises an area under the care contribution curve over a period of time, the period of time ending with the current time.

9. The media of claim 8, wherein creating the care team assignment for the patient comprises comparing the care contribution score for each clinician to a minimum contribution threshold score.

10. The media of claim 1, wherein creating the care team assignment for the patient comprises comparing care contribution scores of at least a first clinician and a second clinician, wherein the first clinician and the second clinician have a common role and a common specialty.

11. The media of claim 10, wherein creating the care team assignment for the patient further comprises assigning the first clinician to a care member spot reserved for the common role and common specialty upon determining the first clinician has a greater care contribution score than the second clinician.

12. The media of claim 1, wherein the method further comprises using the care team assignment to notify at least one care team member of an event associated with the patient.

13. A system for assigning members to a patient's care team, the system comprising:
one more processors;
non-transitory computer storage memory storing computer-usable instructions that, when executed by the one or more processors, implement a method comprising:
receiving, in real-time directly from a device used to perform an action, one or more electronic indicators of an action associated with a first clinician;
receiving, in real-time from the electronic health record or directly from the device used to perform an action, one or more electronic indicators of an action associated with a second clinician, the second clinician having a role and a specialty in common with the first clinician;
generating a first care contribution curve using the one or more electronic indicators of an action associated with the first clinician;
generating a second care contribution curve using the one or more electronic indicators of an action associated with the second clinician;
determining a first care contribution score for the first clinician using the first contribution curve and determining a second care contribution score for the second clinician using the second contribution curve;
comparing the first care contribution score and the second care contribution score; and
assigning the first clinician as a member of the patient's care team upon determining the first care contribution score is greater than the second care contribution score.

14. The system of claim 13, wherein assigning the first clinician comprises assigning the first clinician as a primary care team member and wherein the method further comprises assigning the second clinician as an alternative care team member.

15. The system of claim 13, wherein further comprises receiving at least one or more additional electronic indicators of actions associated with the second clinician.

16. The system of claim 15, wherein further comprises determining a third care contribution score for the first clinician and a fourth care contribution curve for the second clinician, the fourth care contribution curve being based on at least the one or more additional electronic indicators of actions.

17. The system of claim 16, wherein further comprises:
determining the fourth care contribution score is greater than the third care contribution score;
removing the first clinician from the care team; and
assigning the second clinician to the care team.

18. A computerized method for managing a care team assignment for a patient, the method comprising:
receiving, in real-time directly from a device used to perform an action, a plurality of electronic indicators of actions initiated by a clinician and associated with the patient's care, each electronic indicator including a time the action is taken and at least one clinician associated with the action;
constructing a time series of actions for each clinician associated with the actions;
categorizing each action from the plurality of electronic indicators of actions into a type of action;
categorizing each clinician associated with an action into a clinician role;
assigning a care contribution level as an initial level to each action;
determining a rate of decay of the care contribution level for one or more of the actions associated with each clinician, the rate of decay being based on the type of action and the clinician role;
generating care contribution curves for each action using the initial level and the rate of decay;
determining a care contribution score for each clinician using the care contribution curves and the times series; and
determining a care team assignment for the patient based on the care contribution score for each clinician, the care team assignment being a group of one or more clinicians responsible for the patient's care.

19. The computerized method of claim 18, wherein the care contribution curves are generated using a logistic function.

20. The computerized method of claim 18, wherein at least two actions associated with a clinician are taken at the same time and the at least two actions correspond to different rates of decay, wherein determining the rate of decay includes using the rate of decay that results in the maximum care contribution curve.

* * * * *